United States Patent [19]
Rhoad

[11] Patent Number: 5,806,526
[45] Date of Patent: Sep. 15, 1998

[54] EAR PLUGS

[76] Inventor: Don F. Rhoad, 245 Berte Carter Dr., Bamberg, S.C. 29003

[21] Appl. No.: 693,962

[22] Filed: Aug. 7, 1996

[51] Int. Cl.⁶ .................................................. A61F 11/00
[52] U.S. Cl. ......................... 128/864; 128/857; 128/858
[58] Field of Search ................................. 128/864–868; 181/129, 130, 134, 135

[56] References Cited

U.S. PATENT DOCUMENTS

| | | |
|---|---|---|
| D. 241,881 | 10/1976 | Peterson et al. . |
| D. 338,267 | 8/1993 | Scholey . |
| 4,219,018 | 8/1980 | Draper .................................... 128/864 |
| 4,321,998 | 3/1982 | Van de Walker ....................... 128/864 |
| 4,344,425 | 8/1982 | Strauss .................................... 128/864 |
| 4,896,380 | 1/1990 | Kamitani . |
| 5,074,375 | 12/1991 | Grozil . |
| 5,086,789 | 2/1992 | Tichy . |
| 5,483,975 | 1/1996 | Hirschenbain . |

FOREIGN PATENT DOCUMENTS 608059  9/1948  United Kingdom .

*Primary Examiner*—Michael A. Brown

[57] ABSTRACT

A pair of ear pugs that are attached to eyeglasses or safety goggles by a cord. The ear plugs, which are preferably made of foam or some other deformable material, can attach to each other. When the ear plugs are connected to each other, they, along with the cords attached to them, form a continuous strap for holding on a pair of glasses. This in-line arrangement allows a pair of ear plugs and their attached cords to function as a lanyard when the ear plugs are not in use. This arrangement in which the ear plugs can be separated provides a breakaway lanyard as required by OSHA for safety and reduces the chance of injury due to the lanyard becoming entangled in machinery. This arrangement also eliminates the requirement for separate cords and reduces the likelihood of lost ear plugs.

12 Claims, 3 Drawing Sheets

EAR PLUGS

BACKGROUND OF THE INVENTION

1. Field of the Invention

The present invention relates to ear plugs generally, and more specifically, to glasses-attached ear plugs which attach to each other when not in use.

2. Description of the Prior Art

The present invention pertains to a set of ear plugs that attach together. The ear plugs are preferably attached to a pair of eyeglasses, which can be sunglasses or safety glasses, by cords, one for each ear plug. The attachment of the ear plugs completes a continuous cord, and forms a lanyard for the glasses.

U.S. Pat. No. 4,896,380, issued on Jan. 30, 1990 to Shigeki Kamitani, and U.S. Pat. No. 5,074,375, issued on Dec. 24, 1991 to Richard S. Grozil, teach ear plugs attached to a face mask or glasses by a tube or a cord. U.S. Pat. No. Des. 241,881, issued on Oct. 12, 1976 to Robert M. Peterson et al., and U.S. Pat. No. Des. 338,267, issued on Aug. 10, 1993 to Michael F. Scholey, show ear plugs connected to one another by a cord. Other cited patents teach spectacles or hearing protection in combination with goggles.

None of the above patents, taken either singly or in combination, is seen to describe the instant invention as claimed.

SUMMARY OF THE INVENTION

The instant invention relates to ear pugs that are attached to eyeglasses or safety goggles by a cord. The ear plugs, which are preferably made of foam, medical grade rubber or plastic, or some other deformable material, can attach to each other. When the ear plugs are connected to each other, they, along with the cords attached to them, form a continuous strap for holding on a pair of glasses. This in-line arrangement allows a pair of ear plugs and their attached cords to function as a lanyard when the ear plugs are not in use. This arrangement in which the ear plugs can be separated provides a breakaway lanyard as required by OSHA for safety and reduces the chance of injury due to the lanyard becoming entangled in machinery. This arrangement also eliminates the requirement for separate cords and reduces the likelihood of lost ear plugs.

Accordingly, it is a principal object of the invention to provide a pair of ear plugs which can be attached to one another.

It is another object of the invention to provide an arrangement such that the attachment of the ear plugs completes a strap around a pair of eyeglasses.

It is an additional object of the invention to provide a breakaway lanyard for safety.

It is a further object of the invention to provide an invention which eliminates an extra cord around a pair of eyeglasses.

Still another object of the invention is to provide a configuration for a set of ear plugs which reduces their likelihood of being lost.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
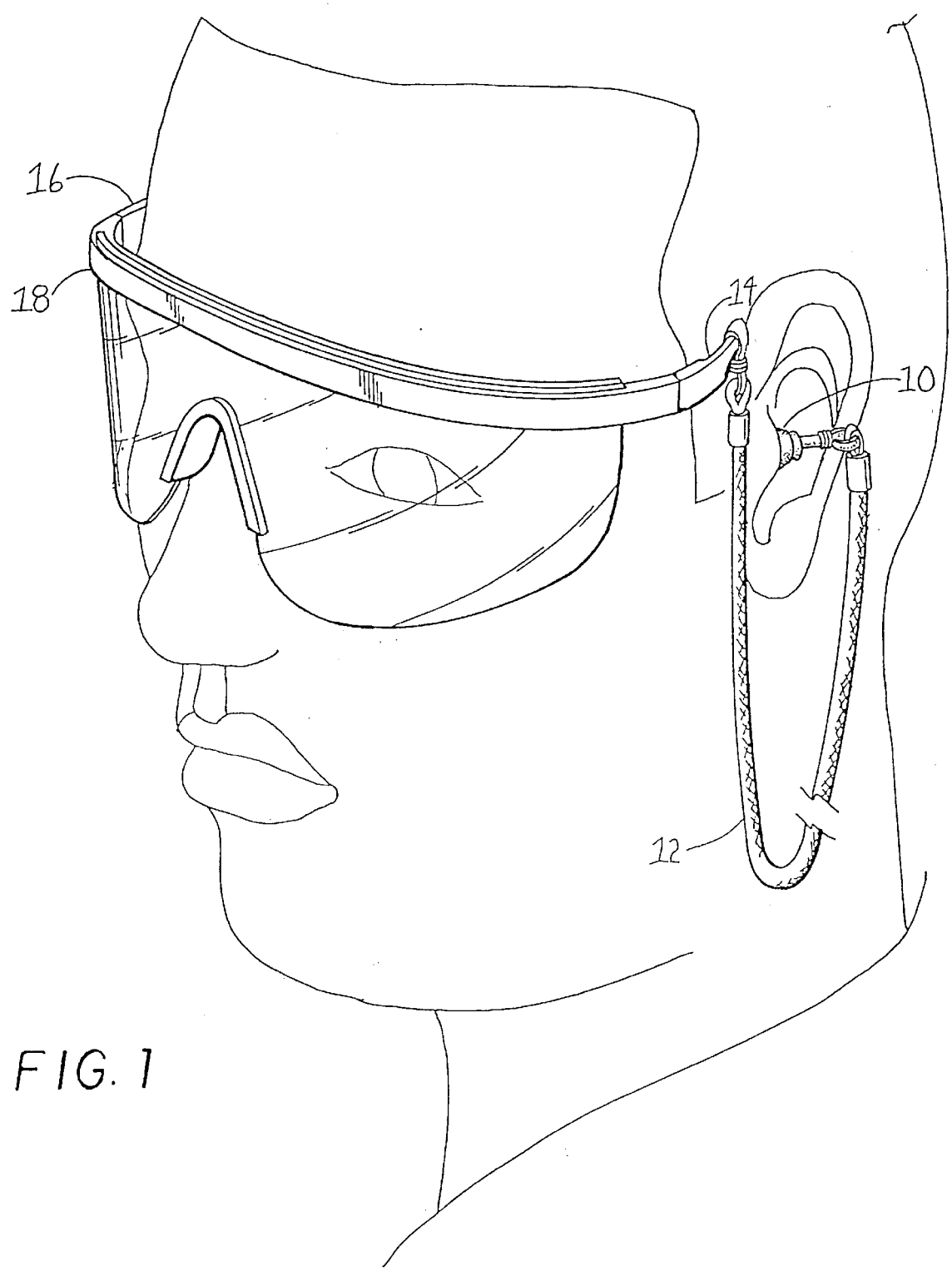
FIG. 1 is an environmental perspective view of the in-line ear plugs attached to a pair of safety glasses.
Figure 2:
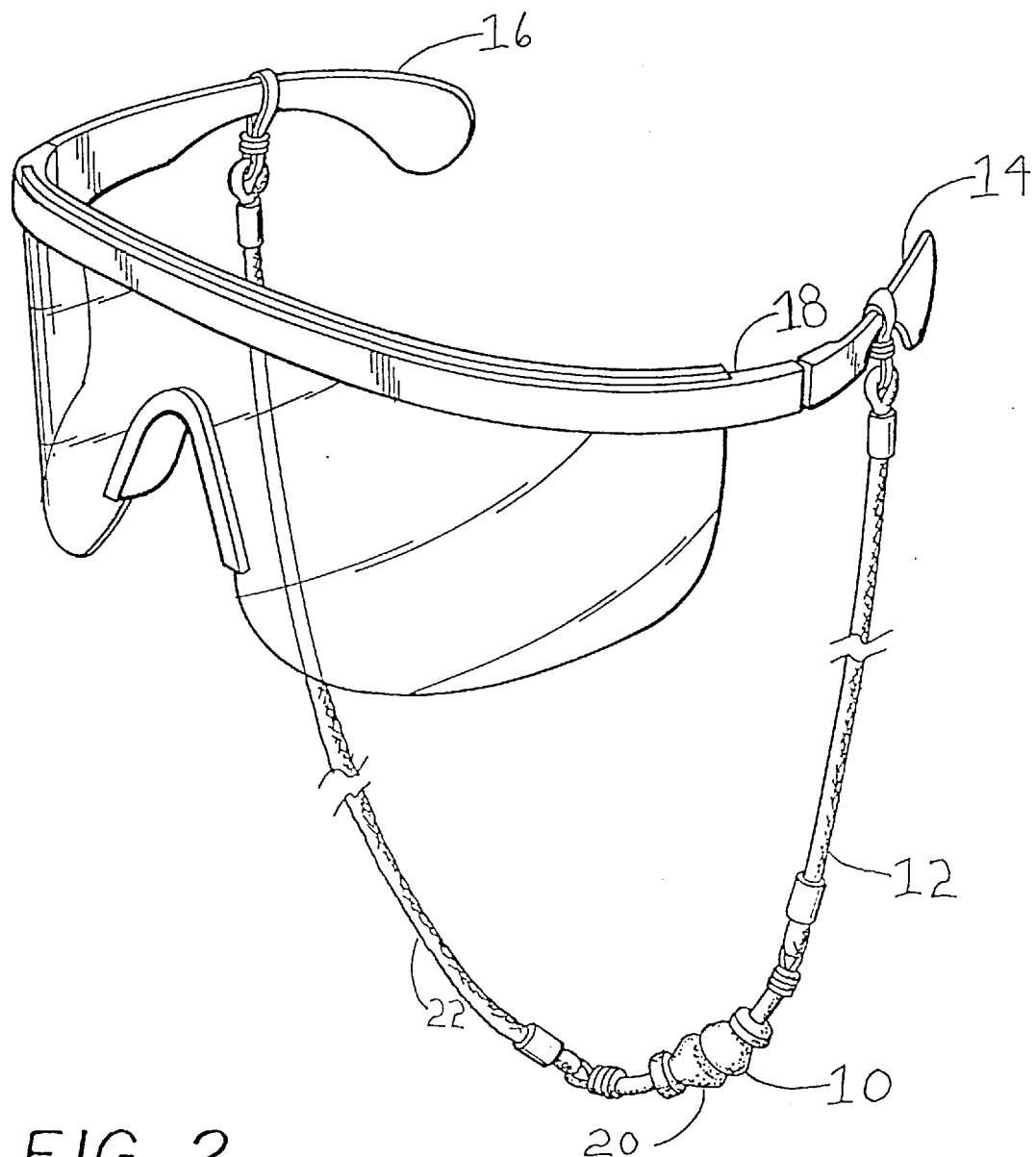
FIG. 2 is a perspective view of the in-line ear plugs with the ear plugs attached to one another simulating a lanyard for a pair of safety glasses.
Figure 3:
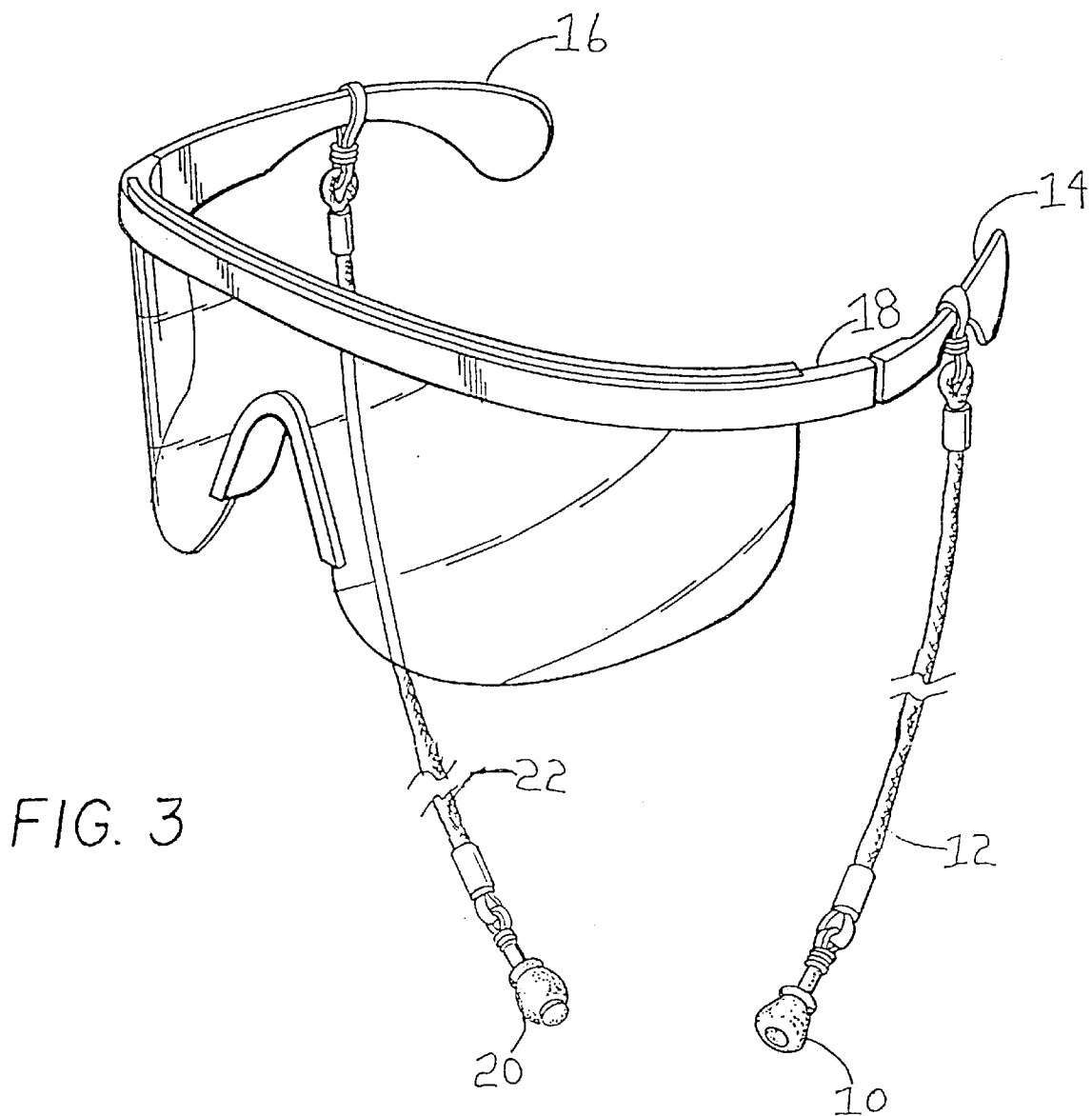
FIG. 3 is a perspective view of the in-line ear plugs with the ear plugs unattached as they would be in use.

The present invention is shown in use in FIG. 1, in which a user wearing safety glasses is also wearing ear plugs attached to the glasses by a cord. As best seen in FIGS. 2 and 3, the left and right ear plugs 10 and 20 are connected to left and right temple pieces 14 and 16 of a pair of safety glasses 18 by left and right cords 12 and 22.

As seen in FIG. 2, when the ear plugs 10 and 20 are attached to one another, they form a continuous, in-line strap around the glasses 18; i.e., the ear plugs 10 and 20 and the cords 12 and 22 form a lanyard for holding on the glasses. Because of this dual function of the ear plugs 10 and 20, the need for an extra cord is eliminated. Further, the likelihood of losing or misplacing or using someone else's ear plugs, an unsanitary situation, is greatly reduced.

FIG. 3 shows the ear plugs 10 and 20 separated and ready for use in the ears. The ear plugs 10 and 20 are made of foam or some other deformable material so that they can readily be inserted into the ear. In the preferred embodiment, the ear plugs 10 and 20 are attached to cords 12 and 22. However, any type of flexible elongated element, such as rope, string, or chain, can hold the ear plugs 10 and 20 and be used in the formation of a lanyard.

Figure 4:
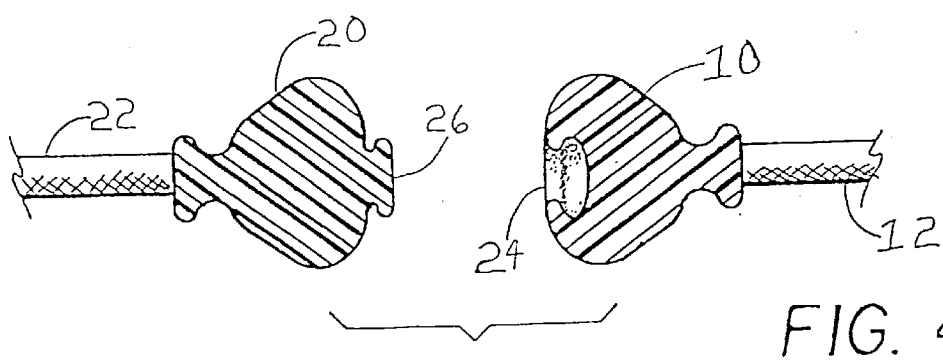
FIG. 4 is a detailed, sectional view of the ear plugs showing the protrusion and hole which allow the ear plugs to mate.

The details of the mating of the ear plugs 10 and 20 are seen in FIG. 4, in which an example of a ball and socket connection is shown. However, any known type of connection can be used, for example hook and loop fasteners, steel or plastic snaps, twist connectors, magnetic fasteners, or another type of ball and socket connection. One of the ear plugs contains a hole 24 for receiving a protrusion 26 on the other ear plug. This placement of the protrusion 26 in the hole 24 attaches the ear plugs 10 and 20 and completes a strap around the glasses 18.

The instant invention is a great benefit for one who is required to wear safety glasses, for example one in an industrial setting. Carrying the ear plugs on the glasses and fastening them to form a lanyard for the glasses is convenient in allowing one to always know the whereabouts of the ear plugs. Because the lanyard will separate, i.e. the ear plugs will break away from each other, it can be safely worn in an industrial setting. Additionally, the ear plugs will be in a position where they can readily be used.

It is to be understood that the present invention is not limited to the sole embodiment described above, but encompasses any and all embodiments within the scope of the following claims.

I claim:

1. A pair of ear plugs comprising a first ear plug having a body that has a first end and a second end, said body adapted to be placed into a first ear and a second ear plug having a body that has a first end and a second end adapted to be placed in the order ear, each said ear plug body having complementary releasably mating connection means at the first end which facilitates the connecting and disconnecting of said bodies and a second connection means at the second end which is adapted to be connected to safety glasses.

2. The ear plugs of claim 1, wherein one of said ear plug bodies has means defining a hole and the other of said ear plug bodies has a protrusion, and mating is accomplished by fitting said protrusion into said hole.

3. The ear plugs of claim 2, wherein said connection mean further comprising a flexible elongated element, each said ear plug body being attached to said flexible elongated element.

4. The ear plugs of claim 3, wherein said flexible elongated element is a cord.

5. The ear plugs of claim 1, wherein said connection means further comprising a flexible elongated element, each said ear plug body being attached to said flexible elongated element.

6. The ear plugs of claim 5, wherein said flexible elongated element is a cord.

7. For use with eyeglasses having a pair of temple pieces, a pair of ear plugs and a flexible elongated element attachable to the temple pieces of eyeglasses, said pair of ear plugs further comprising a first ear plug having a body that has a first end and a second end, said body adapted to be placed into a first ear and a second ear plug having a body that has a first end and a second end adapted to be inserted in a second ear, each said plug body having a complementary releasably connection means at said first end which facilitates the connecting and disconnecting of said bodies and said flexible elongated element at said second end which is adapted to be connected the temple pieces of eyeglasses.

8. The combination of claim 7, wherein one of said complementary releasably mating connection means of said ear plug bodies defines a hole and the other of said complementary releasably mating connection means of said ear plug bodies defines a protrusion, and mating is accomplished by fitting said protrusion into said hole.

9. The combination of claim 8, wherein said flexible elongated element is a cord.

10. The combination of claim 7, wherein said flexible elongated element is a cord.

11. The combination of claim 7, further comprising a pair of eyeglasses, and wherein said eyeglasses are one of safety glasses or safety goggles.

12. The combination of claim 7, further comprising a pair of eyeglasses, and wherein said eyeglasses are sunglasses.

* * * * *